United States Patent
Kerr-Conte et al.

(10) Patent No.: US 6,900,051 B2
(45) Date of Patent: May 31, 2005

(54) PROCESS FOR OBTAINING MAMMALIAN INSULIN SECRETING CELLS IN VITRO AND THEIR USES

(75) Inventors: Julie Kerr-Conte, Lambersart (FR); Françoise Pattou, Lambersart (FR)

(73) Assignee: Centre Hospitalier Regional Universitaire De Lille, Lille Cedex (FR)

(*) Notice: Subject to any disclaimer, the term of this patent is extended or adjusted under 35 U.S.C. 154(b) by 154 days.

(21) Appl. No.: 09/960,632

(22) Filed: Sep. 21, 2001

(65) Prior Publication Data

US 2002/0155598 A1 Oct. 24, 2002

(30) Foreign Application Priority Data

Feb. 10, 2000 (FR) .............................. 00 12547

(51) Int. Cl.⁷ ................................ C12N 5/00
(52) U.S. Cl. ................ 435/366; 435/325; 435/378; 435/379; 435/380; 435/381
(58) Field of Search ................ 435/325, 366, 435/378, 379, 380, 381

(56) References Cited

FOREIGN PATENT DOCUMENTS

| WO | WO 00/46351 | 8/2000 |
|----|-------------|--------|
| WO | WO 00/78929 | 12/2000 |

OTHER PUBLICATIONS

Gmyr, et al., "Adult human cytokeratin 19–positive cells reexpress insulin promoter factor 1 in vitro", Diabetes 49 (2000) pp. 1671–1680.

Gmyr, et al., "Discarded exocrine tissue may be a potential source of human pancreatic precursors", Acta Diabetologica 37 (2000) p. 153.

Bonner–Weir, et al., "In vitro cultivation of human islets from expanded ductal tissue", Proceedings of the National Academy of Sciences of the United States 97 (2000) pp. 7999–8004.

Gmyr, et al., "Expansion of human ductal pancreatic stem cells obtained from main duct, purified islet preparation, or exocrine tissue", Acta Diabetologica 34 (1997) p. 107.

Kerr–Conte, et al., "Model for islet cell neogenesis from adult human pancreatic ductal epithelium in vitro", Experimental and Clinical Endocrinology & Diabetes 105 (1997) pp. A28–A29.

Gmyr, et al., "Human pancreatic ductal cells: Large–scale isolation and expansion", Cell Transplantation 10 (2001) pp. 109–121.

Primary Examiner—Leon B. Lankford, Jr.
(74) Attorney, Agent, or Firm—Hoffman & Baron, LLP; Irving N. Feit

(57) ABSTRACT

The present invention relates to a process for obtaining mammalian insulin secreting cells in vitro, characterized in that it contains the following steps: a) preparation of the mammalian pancreatic tissues by removal of a pancreas, b) dissociation of the pancreatic tissues obtained in step (a) into isolated pancreatic cells, c) possibly the elimination of the endocrine cells from the pancreatic cells isolated in step (b), d) induction of dedifferentiation of the cells isolated in step (b) into ductal precursor cells, e) induction of redifferentiation of the ductal precursor cells obtained in step (d) into insulin secreting cells. It also concerns the use of the insulin secreting cells thus obtained for the preparation of a pharmaceutical composition which can be used for the treatment of pancreatic pathologies and particularly diabetes.

31 Claims, 5 Drawing Sheets

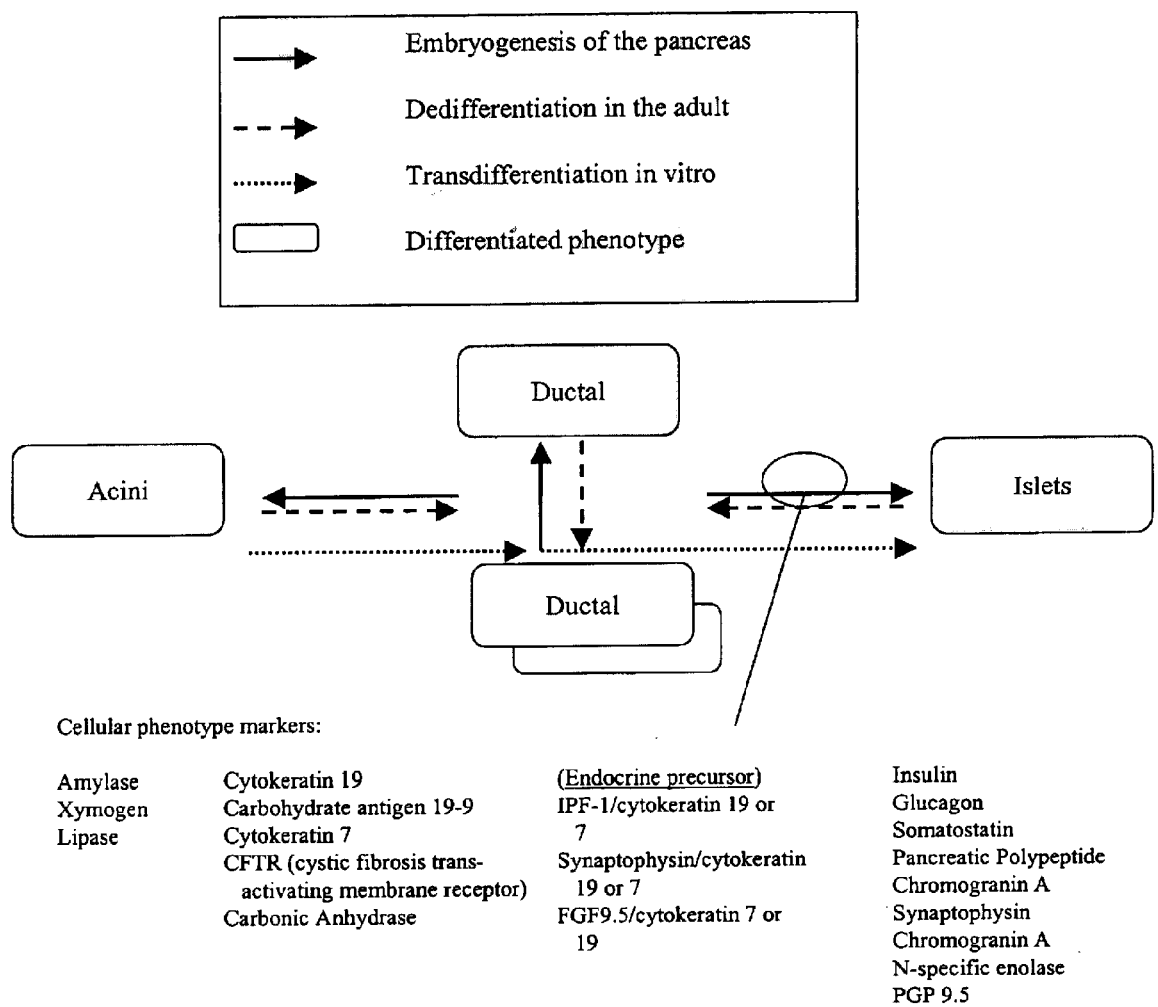
Figure 1. Neogenesis of the pancreatic cells and cellular phenotype markers

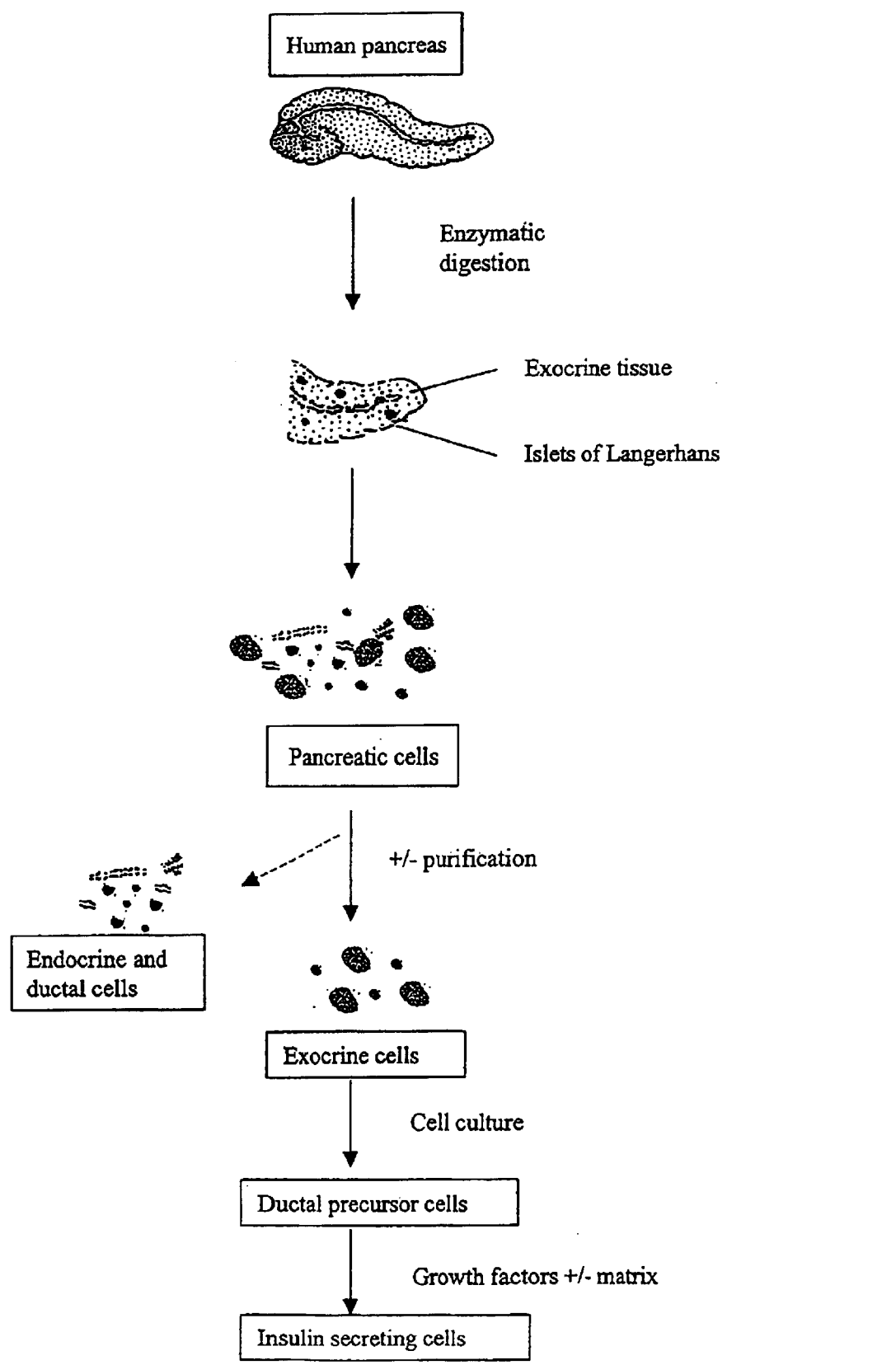
Figure 2. Diagram of the process of preparation of insulin secreting cells Figure 3. Protein expression during 14 days of culture of the human exocrine preparations (A and B, mean ± SEM based on n=5)
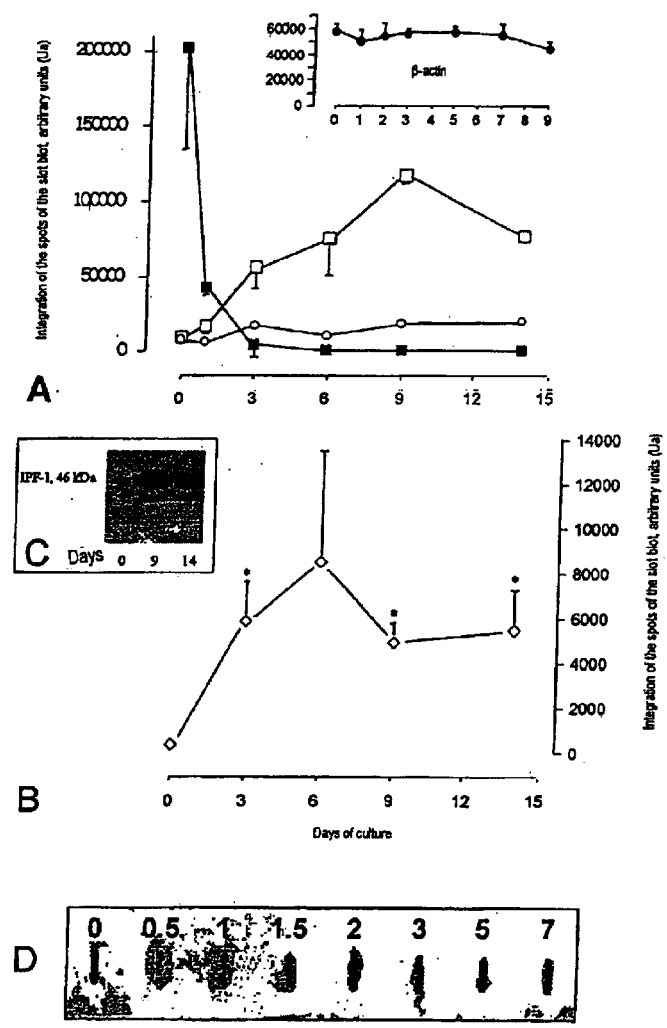

Figure 4. RT-PCR analyses on the expression of IPF-1 in the course of culturing of the preparations
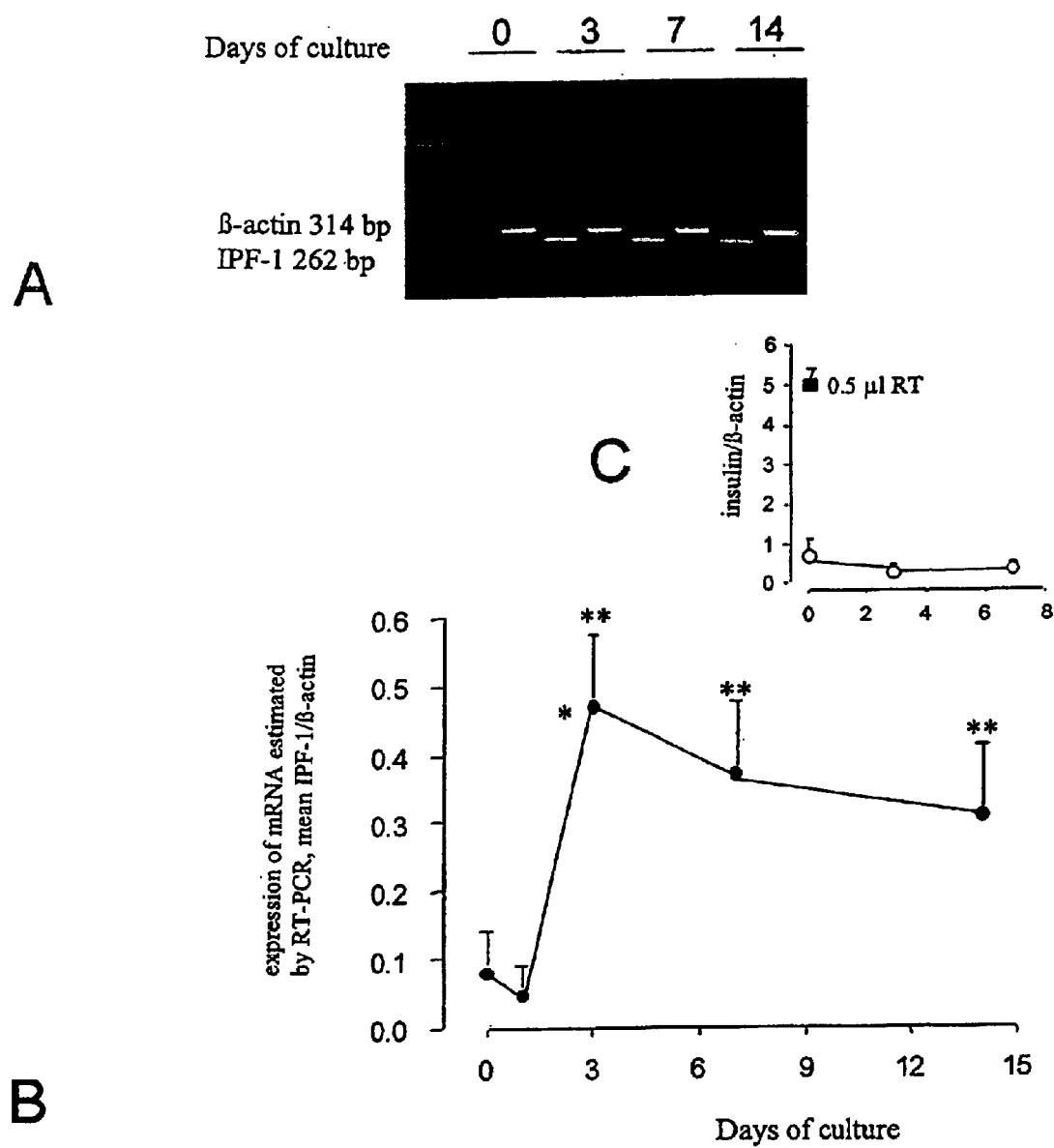

Figure 5. Characterization by immunohistochemistry of the phenotype of the ductal precursor cell cultures. The bar represent 100 μm.
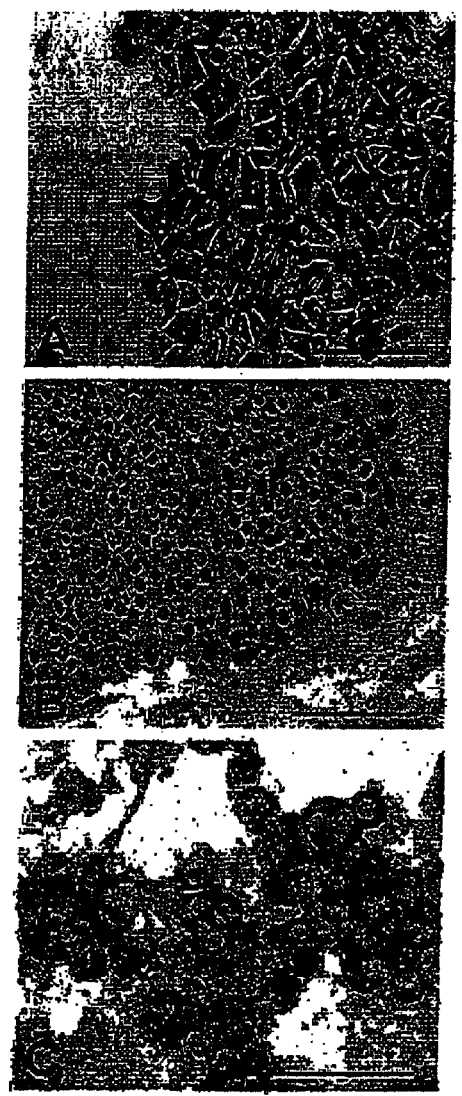

PROCESS FOR OBTAINING MAMMALIAN INSULIN SECRETING CELLS IN VITRO AND THEIR USES

The present invention concerns a process for obtaining insulin secreting cells in vitro from pancreatic tissue. It particularly concerns obtaining insulin secreting cells from pancreata of patients suffering from pancreatic pathologies and particularly diabetes. It also concerns the use of these cells for preparations intended for therapeutic treatment of diabetes.

Cellular therapy is currently offering important perspectives in the treatment of diabetes (Shapiro A. M. et al. Islet transplantation in seven patients with type 1 diabetes mellitus using a glucocorticoid-free immunosuppressive regimen. N Engl J Med 343:230–238, 2000). The concept of treatment of diabetes by ectopic transplantation of insulin secreting cells has already been validated. In the course of a total pancreatectomy, isolation and intraportal transplantation of the endocrine islets of the pancreas make it possible to maintain endogenous, almost physiological, secretion of insulin and to maintain glucide homeostasis for more than ten years (Pyzdrowski, K. L., et al. Preserved insulin secretion and insulin dependence in recipients of islet autografts. New England J. Med. 1992, 327:220–226).

However, in spite of numerous technical advances, the insufficient and often random yield from isolation of the islets remains a major hindrance to the development of cellular therapy for diabetes. Currently, the assembly of islets coming from several donors is still most often necessary in order to transplant a sufficient mass of endocrine tissue in a diabetic patient, and given the limited number of available donors, the current use of primary human islets of Langerhans nevertheless prohibits any hope of large scale development of cellular therapy for this disease.

Thus, new alternative processes for obtaining insulin secreting cells which are less limiting and which can be used in humans have been envisaged, such as genetic manipulation of somatic cells in order to induce synthesis of insulin, immortalizing of cell lines or use of animal cells. However, there are still problems because on one hand the coordinated transcriptional regulation of insulin secretion is complex, and on the other hand clinical use of transformed cells of animal origin is very controversial. Consequently, the design of alternative methods for obtaining insulin secreting cells remains a major stake in the context of cellular therapy for diabetes.

Another approach takes into account the recent experimental studies which have revealed in the adult pancreas the presence of pancreatic stem cells which are capable of proliferation and differentiation.

It is known that the pancreas forms from the endoderm during embryonic development (Le Douarin, N. M. On the origin of pancreatic endocrine cells. Cell, 1988, 53:169–171) and that the three existing pancreatic cell types are derived from the proliferation of the pancreatic epithelium and its secondary differentiation into ductal, endocrine or acinar tissue.

Although the mechanisms of differentiation between the different pancreatic cell types have not been completely elucidated, certain specific phenotypic markers of each of them are known. Thus in rodents as in humans the phenotype of the pancreatic stem cells is of the ductal type as demonstrated by the expression by them of cytokeratins 20 and 19 (Bouwens L. et al. Cytokeratins as markers of ductal cell differentiation and islet neogenesis in the neonatal rat pancreas. Diabetes. 1994, 43:1279–1283; Bouwens L. et al. Proliferation and differentiation in the human fetal endocrine pancreas. Diabetologia, 1997, 40:398–404).

Also known is the phenomenon called nesidioblastosis, whose mechanism remains unknown, which reproduces in the adult period the mode of embryonic formation of the endocrine cells of the pancreas. Nesidioblastosis is not a species specific phenomenon; moreover, it is also observed in humans in certain pathological circumstances. Nesidioblastosis is also frequent in the adjacent parenchyma of endocrine tumors of the pancreas, whether they are sporadic or caused by mutation of a tumor suppressing gene, in cases of endocrine neoplasia. In certain exceptional cases, diffuse neosidioblastosis [sic; nesidioblastosis] of the whole pancreas can even be observed.

These observations therefore suggest the persistence in the mature human pancreas of quiescent stem cells with a ductal phenotype which are capable of endocrine differentiation under certain conditions.

Processes for in vitro culturing of adult pancreas cells which make use of these observations and reproduce this phenomenon of nesidioblastosis in vitro have already been described. For example, the European patent applications EP 758376 and EP 871455 describe a process for obtaining insulin secreting cells from pancreatic preparations of adult tissue enriched with stem cells.

However, the process for obtaining insulin secreting cells described in these documents has several problems. On one hand, it includes a first culture step intended for stem cell enrichment of the pancreatic cell population isolated during the first step of the process. This step, spread out over several weeks, provides for the culturing of the pancreatic cells in a serum-poor medium so as to eliminate 99% of the pancreatic cells, the majority of which are differentiated exocrine cells. The aim is to maintain in culture only a cell population which is enriched with islet precursor stem cells. After having carried out this selection, the small population of isolated stem cells undergoes an expansion step for several weeks. The third step of the process involves the differentiation of the stem cells into insulin secreting cells. Another major problem inherent to this process lies in the small number of stem cells which can be obtained after having eliminated almost all (99%) of the differentiated pancreatic cells. This process for obtaining endocrine islets in vitro in adult mammals reproduces the route of pancreatic embryogenesis as it occurs in vivo.

In the context of the present invention, the inventors succeeded for the first time in vitro in inducing a transdifferentiation of differentiated pancreatic exocrine cells to another differentiated phenotype. This transdifferentiation is not based on the physiological route followed by pancreatic embryogenesis in vivo and thus opens up an alternative way to obtain differentiated pancreatic cells.

In a completely surprising manner, the inventors succeeded in inducing in vitro a dedifferentiation of the exocrine cells of the adult pancreas, constituting more than 95% of the pancreatic parenchyma, under certain culture conditions, in order to obtain dedifferentiated cells, hereafter called ductal precursor cells.

These ductal precursor cells are in turn grown in a suitable medium in which redifferentiation is induced, which transforms them into insulin secreting endocrine cells.

In the context of the present invention, the following meanings are understood:

Differentiation: for a cell, the act of acquiring a specialized function. This is the process which leads to the expression of characteristic phenotypic properties of a functionally mature cell in vivo.

Redifferentiation: for a cell, the act of reacquiring a specialized function which it previously lost following dedifferentiation.

Dedifferentiation or retrodifferentiation: for a specialized cell, the act of regressing to a less specialized embryonic form. Dedifferentiation entails the loss, temporary or definitive, of the differentiated genotypic and/or phenotypic characteristics which said specialized cell was able to acquire during its development. Dedifferentiation is either an adaptive process implying that the differentiated phenotype can be attained by administering the suitable inducers, or a selective process, in that case implying that the precursor cells were chosen because of their high proliferation potential.

Transdifferentiation: This is a biological process of reprogramming of the genetic expression from one cell phenotype to another. Transdifferentiation includes a first step of dedifferentiation and a second step of redifferentiation.

Stem cell: Cell which has unlimited self-replication capacities, which is capable of producing at least a highly differentiated lineage of unipotential/bipotential/multipotential/pluripotential/totipotential cells.

Dedifferentiated cell: any cell which does not express the phenotype of the original cell or that of the subsequent differentiated cells.

Epithelial precursor cell: Cell which is capable of differentiating, but only in order to become a cell belonging to its own epithelial tissue type and not to another. The ductal precursor cells belong to this category.

Beta-cell: cell of the islets of Langerhans of the pancreas which secretes the hormone insulin in response to glucose and other secretagogues.

The inventors carried out extensive research studies in order to prove from the molecular standpoint as well as from the protein standpoint that, under suitable culture conditions, the pancreas exocrine cells dedifferentiate into precursor cells bearing a characteristic phenotype of the ductal epithelial cells. Later redifferentiation of these exocrine precursor cells under suitable culture conditions makes possible the preparation of insulin secreting cells in large quantity, with said ductal epithelial cells reexpressing the factor IPF-1, a specific marker of the insulin secreting beta-cells.

Manifestations in vivo of this cellular dedifferentiation had already been observed in vitro, but the inventors reproduced it in vitro for the first time and used it for the purpose of obtaining an abundant source of endocrine precursor pancreatic cells. The process which they used opens the way to great clinical innovations in the domain of therapeutic treatment of pancreatic pathologies, particularly diabetes. The new process for obtaining insulin secreting cells by transdifferentiation used in the context of the invention provides an abundant source of precursors of beta-cells. This makes it possible to easily envisage on one hand an allogenic therapy for the pancreatic pathologies, particularly of diabetes, and on the other hand an autologous cellular therapy. In effect, a partial pancreatectomy by the process of the invention will allow one to produce from a small fragment of the pancreas of the patient autologous insulin secreting cells in sufficient quantity to restore the pancreatic functions.

The present invention uses a process for obtaining insulin secreting cells in vitro starting from a preparation of pancreatic cells of an adult pancreas, which is possibly devoid of endocrine cells.

The process for obtaining insulin secreting cells of the invention is remarkable because it is carried out precisely using the exocrine cell population which counts for more than 95% of the cells present in the pancreatic tissue, and not using isolated stem cells only.

It is thus possible by this route to obtain up to 1.5 billion ductal precursor cells from a single human pancreas, or 100,000 times more than from the pancreatic ducts themselves.

Thus, the invention relates to a process for obtaining mammalian insulin secreting cells in vitro, characterized in that it contains the following steps:

a) preparation of the mammalian pancreatic tissues by removal of a pancreas, b) dissociation of the pancreatic tissues obtained in step (a) into isolated pancreatic cells, c) possibly, elimination of endocrine cells from the isolated pancreatic cells obtained in step (b), d) induction of dedifferentiation of the cells isolated in step (c) into ductal precursor cells, e) induction of redifferentiation of the ductal precursor cells obtained in step (d) into insulin secreting cells.

According to a preferred embodiment of the process of the invention, the dissociation of the pancreatic tissues in step (b) is carried out by means of enzymatic digestion.

Advantageously, the pancreatic cells isolated in step (b) are devoid of endocrine cells in step (c) before step (d) of induction of differentiation [sic; dedifferentiation].

Advantageously, the elimination of the endocrine cells from the pancreatic cells of step (c) is carried out by means of density gradient centrifugation.

Preferably, the elimination of the endocrine cells from the pancreatic cells in step (c) is carried out by withdrawal of the fraction of endocrine cells recovered in the density range between 1.027 g/L to 1.104 g/L, preferably between 1.045 g/L to 1.097 g/L.

Quite preferably, the pancreatic cells devoid of endocrine cells obtained in step (c) are exocrine cells recovered in the density gradient residue.

According to another embodiment of the process of the invention, the elimination of the endocrine cells in step (c) is carried out by means of a cell separator.

Advantageously, the dedifferentiation of step (d) includes the following substeps:

i) culturing of the cells obtained in step (c) with a cell concentration between $1 \times 10^6$ and $10 \times 10^6$ cells/mL, preferably between $2 \times 10^6$ and $6 \times 10^6$ cells/mL, in a culture medium containing:

glucose at a concentration between 1 and 10 g/L, preferably between 2 and 5 g/L.

possibly serum, chosen from fetal calf serum, bovine serum or human serum, at concentrations greater than 8%, preferably between 10 and 15% final volume.

a mixture of insulin, transferrin, selenium used at a concentration between 0.2 and 3%, preferably between 1.0 and 2.5%, possibly factors stopping the growth of fibroblasts at a concentration between 20 and 100 µg/mL, preferably between 30 and 60 µg/mL, possibly antibiotics, antifungal agents, for a duration between 4 to 9 days, preferably 5 to 7 days, ii) recovery of the ductal precursor cells obtained in step (i).

Advantageously, the induction of the redifferentiation of step (e) includes the following substeps:

1) possibly the separation of the ductal precursor cells obtained in step (d)

ii) culturing of the ductal precursor cells obtained in step (i) at cell concentrations between $3.5 \times 10^5$ cells 25/cm² and $4 \times 10^6$ cells/25 cm$^2$, preferably $7 \times 10^5$ cells/25 cm$^2$ to $3 \times 10^6$ cells/25 cm$^2$, in a culture medium containing:

glucose at concentrations between 1 and 10 g/L, preferably between 2 and 5 g/L.

possibly serum, chosen from fetal calf serum, bovine serum or human serum, at concentrations greater than 2.5%, preferably between 5 and 15% final volume.

possibly a mixture of insulin, transferrin, selenium at a concentration between 0.2 and 5%, preferably between 0.5 and 2%, possibly antibiotics and antifungal agents, possibly in the presence of a matrix, for a duration between 12 and 36 h, iii) withdrawal of said culture medium and of the non-adherent cells possibly present, iv) culturing of the cells obtained in step (iii) in a culture medium such as that used in step (i), possibly containing growth factors, for a duration between 4 and 12 days, preferably between 5 and 10 days, in order to obtain insulin secreting endocrine cells, and v) recovery of the insulin secreting cells obtained in step (iv).

According to a preferred implementation of the process of the invention, the separation of the cells in substep (i) of step (e) is done with trypsin/EDTA at concentrations between 0.01 and 0.1% of trypsin, preferably 0.015–0.03, and EDTA between 0.1 and 1 mM, preferably 0.25–0.75 mM.

According to a preferred embodiment of the process of the invention, the matrix used for the culturing of the cells in substep (ii) of step (e) is chosen from collagen type IV, 804G, collagen type I, Matrigel or its equivalents which are known to the expert in the field.

Advantageously, the pancreatic tissues dissected in step (a) are obtained from the pancreas of a brain dead adult human.

Preferably, the pancreatic tissues dissected in step (a) are obtained from a fragment of a pancreas of a living patient suffering from a pancreatic pathology and quite preferably from a fragment of a pancreas of a living patient suffering from diabetes.

The invention also concerns insulin secreting cells prepared by the process of the invention.

The invention also concerns the use of the insulin secreting cells prepared by the process of the invention for the manufacturing of a pharmaceutical composition intended for the treatment of human pancreatic pathologies, and more particularly intended for the treatment of diabetes.

The subject of the invention is also a method of administration of the insulin secreting cells prepared according to the process of the invention by means of a percutaneous intraportal catheter.

The subject of the invention is also a bioartificial pancreas made up of insulin secreting cells prepared according to the process of the invention grown after microencapsulation according to processes which are known in themselves to the expert in the field.

The inventors carried out extensive studies aiming to prove that a population of non-beta 1 exocrine pancreatic cells can be effectively obtained in vitro from exocrine pancreatic tissue.

In the first place, the proof of the cellular dedifferentiation in vitro of the pancreatic exocrine cells in a suitable culture medium was supplied by verification of the almost complete loss of amylase expression and an increase of the expression of ductal markers (cytokeratin 19, cytokeratin 7, carbohydrate antigen 19-9).

For the first time, the studies carried out by the inventors demonstrated a reexpression of the insulin promotor factor-1 (IPF-1) or of its equivalents: the pancreatic duodenal homeotic sequence (PDX-1), the islet duodenal homeotic sequence 1 (IDX-1), the somatostatin transactivation factor 1 (STF-1) by the pancreatic cell cultures in the protein and mRNA.

The factor IPF-1 is a homeodomain protein essentially present in the differentiated beta-cells of the adult pancreas (Ohlsson H. et al. IPF-1, a homeodomain-containing transactivator of the insulin gene. The EMBO journal, 12:4251–4259, 1993), functioning as principal regulator of phenotype b.

The expression of IPF-1/PDX-1 is preserved in human beta-cells which have lost their capacity to express insulin after a 30,000 fold expansion.

During the pancreatic ontology, the expression of the factor IPF-1 in the primitive ducts appears to be essential for the formation of endocrine and exocrine cells in mice (Johnson J. et al. Insulin-promoter-factor 1 is required for pancreas development in mice. Nature 371:606–609, 1994); and in humans (Stoffers D. A. et al. Pancreatic agenesis attributable to a single nucleotide, deletion in the human IPF1 gene coding sequence. Nat. Genet. 15:106–110, 1997), its absence leads to pancreatic agenesis. The factor IPF-1 is also reexpressed in a significant manner in the ductal cells in the course of proliferation during pancreatic regeneration in adult rodents. The authors recently observed the expression of IPF-1 in adult human pancreatic ducts of patients with nesidioblastosis. Consequently, the factor IPF-1 proves to be a marker of the ductal cells which recover their pluripotentiality in order to redifferentiate later into any pancreatic cell type (Sharma A. et al. The homeodomain protein IDX-1 increases after an early burst of proliferation during pancreatic regeneration. Diabetes 48:507–513, 1999).

Given that the expression of the factor IPF-1 in adult ductal cells seems to be a precondition for their redifferentiation into beta-cells in the animal models, the expression of the factor IPF-1 in the human ductal cells in culture provides evidence of their potential redifferentiation and proves that these cells are endocrine precursor candidates.

The later redifferentiation of these endocrine precursor cells under suitable culture conditions will make possible the preparation of the insulin secreting cells in large quantity.

Other advantages and characteristics of the invention will appear upon reading of the examples and figures which follow, reporting the research work which made it possible to verify that, under the culture conditions used, dedifferentiation in vitro of the exocrine pancreatic cells into ductal precursor cells is induced. These ductal precursor cells are then redifferentiated into insulin secreting endocrine cells.

FIG. 1 represents a diagram of the pancreatic embryogenesis with identification of the origin of the different pancreatic tissues and the markers which identify the cellular phenotypic changes used in the context of the invention.

FIG. 2 is a diagram of the process for preparation of insulin secreting cells used in the context of the invention.

FIG. 3 illustrates the phenotypic transition of the cultures which is determined by a slot blot technique.

FIG. 4 shows the expression of the mRNA determined in the exocrine culture preparations.

FIG. 5 illustrates the immunohistochemical analysis by Western Blot, and the PCR-RT results of the exocrine preparations with specific immunolabeling of the ductal antigens CK19, CK7.

HUMAN DUCTAL PRECURSON CELLS

Human cells with a phenotype of ductal precursor cells are obtained in culture from pancreatic preparations. Human pancreata were removed from brain dead adult human donors. The pancreata were possibly weakened with 80 mL of a cold solution of collagenase (0.5 mg/mL, Liberac® or Collagenase of type P, Roche Diagnostics, Meylan, France), diluted in Hanks medium.

The pancreata are dissociated according to the automated method of Ricordi (Ricordi, C. Automated method for isolation of human pancreatic islets. Diabetes 37:413–420, 1988), with some modifications (Kerr-Conte, J. et al. Simple dithizone-stained multilayer test for selection of density gradient before human islet mass purification. Transplant Proc. 26:4013–4015, 1994). After the selection of the densities leading to an optimal separation, the islets are isolated by purification using discontinuous gradient of EuroFicoll® or Histopaque® with a COBE 2991 cell separator.

The exocrine fraction is recovered in the pellet, washed three times in Hanks solution and cultured in a proportion of $2 \times 10^6$ to $6 \times 10^6$ cells per 75 cm$^2$ culture dish in minimum essential Dulbecco culture medium (DMEM, with 3 g/L of glucose), containing 10% fetal calf serum (FCS, Laboratoires Eurobio, Les Ulis, France), 1% insulin, transferrin, selenium (ITS), and 50 µg/mL of Geneticine® (G418) in order to limit the growth of fibroblasts.

After 12 h of attachment and every two/three days the culture medium is changed; the monolayer cultures are maintained for 2 weeks.

Cellular Proliferation

In order to verify cell proliferation estimated in the exocrine preparations, one µCi/mL of tritiated thymidine is added to the culture medium on days 1, 1.5, 2, 3, 4, 6 and 10. The cells thus treated were washed, precipitated with 5% trichloroacetic acid and solubilized in sodium hydroxide (0.5M) and counted in a beta-counter after addition of scintillation liquid to them. The number of counts per minute (cpm) was expressed with respect to the DNA, measured with the PicoGreen® reagent.

RNA

The expression of IPF-1, insulin, and beta-actin were assessed by an RT-PCR reaction using the exocrine cell preparations.

The total RNA was isolated with RNAzol® B and quantified by spectrophotometry (260 nm). The cDNA was synthesized from 2 µg total RNA with oligo(DT)12–18 primers and a reverse transcriptase (M-MLV). The PCR reaction was carried out on an aliquot of one µL of the product of the RT reaction in the presence of 200 mM dNTP, 1.5 mM MgCl$_2$, the primers: 25 pM (IPF-1) or 5 pM (beta-actin) and 5 U AmpliTaq DNA polymerase. The sets of primers include primers for the amplification of IPF-1:

5' C C A T G G A T G A A G T C T A C C - 3 ',
5'-GTCCTCCTCCTTTTTCCAC-3' primers for the insulin:

5'-T G T G A A C C A A C A C C T G T G - 3 ',
5'-CCTCTAGTTGCAGTAGT-3' and primers for the beta-actin:

5'-A T C A T G T T T G A G A C C T C C A A - 3 '
5'-CATCTCTTGCTCGAAGTCCA-3'

The PCR reaction is carried out in a programmable PCR apparatus with 35 cycles for IPF-1 (94° C.: one minute/52° C.: one minute/72° C.: one minute) and with 27 cycles for the insulin (94° C.: 30 sec/53° C.: 1 min/72° C.: 30 sec). All the PCR products are subjected to electrophoresis using 2% agarose gel. After digitalization with a digital camera with integration (CDD) (COHU 4912), the intensities of the bands, expressed in arbitrary units, are quantified by means of the GelAnalysts® software, version 3.01 FR (GreyStone-Iconix). The expression of each specific product is standardized according to the levels of the internal control consisting of the expression of beta-actin.

Protein

A kinetics of expression of amylase, cytokeratin 19, and IPF-1 was done on the protein extracts of the cultures.

For the execution of the slot and Western Blot techniques, the exocrine cells which were grown are trypsinized (0.025% trypsin-5 mM EDTA) in a buffer of Hank's free of Ca++/Mg++ ions (Sigma-Aldrich) and washed in the culture medium. The cells are homogenized in ice in a phosphate-buffered saline (PBS) buffer supplemented with 0.25M glucose and lysed by ultrasound treatment. The protein concentrations were measured with the bicinchinic [sic; bicinchoninic] acid reagent. For the slot blots, the total proteins (25 µg) were deposited on nitrocellulose membranes using the Slot Blot Filtration manifolds filtration apparatus (Amersham Life Science). The membranes were saturated with 5% milk in PBS, incubated with antibodies directed against amylase, chromogranin A, factor IPF-1, cytokeratin CK19, in a diluted (1:10) saturation buffer for two hours. The membranes were then washed twice with PBS and incubated with a solution containing a secondary antibody marked with horseradish peroxidase diluted 1/2000 in the diluted (1/10) saturation solution for one hour. After washing in PBS, the binding of the antibodies is visualized with the reagent for augmentation of the luminescence (ECL® Kit, Amersham). The intensities of the spots were quantified with the Image quant 5.0 apparatus (Molecular Dynamics) and expressed in arbitrary units (Phosphoimager). For the Western Blot, a total quantity of 50 µg of protein was separated by electrophoresis in polyacrylamide gel containing 10% sodium dodecyl sulfate and transferred onto a polyvinylidene fluoride membrane (PVDF, Amersham). The saturation of the membranes and the immunochemoluminescence reaction were carried out as described in the preceding.

Immunohistochemistry

The immunohistochemistry was analyzed on cells fixed in 80% cold ethanol (−20° C., 10 min), with cytocentrifuges, fixed in 1% paraformaldehyde (PFA) or on paraffin sections of pancreatic tissue fixed immediately after collection in 10% formalin or PFA.

The antibodies (IPF-1, cytokeratin 19 and 7, insulin, chromogranin A) are revealed with the Envision® system (Dako), using various chromogenic substrates, 3,3'-diaminobenzidine (DAB), 3-amino-9-ethylcarbazole (AEC), or PhThaloBlue (HistoMark BLUE®). The nuclei were counterstained with Carazzi's hematoxylin.

Apoptosis

The specific cellular apoptosis of the acini is evaluated after immunolabeling with antiamylase antibodies visualized with a biotinylated goat antibody directed against the rabbit antibodies (KPL, Gaithersburg, Md., USA) and streptavidin conjugated with fluorescein isothiocyanate (streptavidin-FITC) (Sigma-Aldrich). The apoptotic nuclear alterations are visualized with Hoechst 33258 (5 µg/mL 10 min, 37° C., Sigma-Aldrich).

Selective Adherence of the Cells

In order to exclude nonacinar cells from preferentially adhering, the amylase positive cells were counted in dishes with respect to the total number of cells (nuclei) before and after 12 h of culture.

The number of acinar cells in the growing fraction is determined by double labeling of cytocentrifuged cells after 12 h and 2 days of culturing with amylase and Ki-67, which labels the cells in all phases of their growth cycle with the exception of the cells in G0 phase.

Results

The human exocrine cell clusters adhere after 12 h of culture and gradually spread out to form monolayer cultures. The cell proliferation, determined by incorporation of tritiated ($^3$H) thymidine, increases rapidly, with a peak after three days and only after a slow decrease of expansion. The incorporation of ($^3$H) thymidine expressed in cpm/µg DNA× $10^3$±[sic; font conversion error] SEM (n=3) is: 40.5±8.7 (day 1), 79.3±24.2 (day 1.5), 83.7±12.8 (day 2), 95.4±5.4 (day 3), 82.1±5.0 (day 4), 42.9±21.5 (day 6) and 68.5±5.1 (day 10).

The DNA and protein levels correlate with the levels of proliferation with tritiated thymidine. FIG. 3 illustrates the phenotypic transition of the cultures determined by slot blot using 25 µg of total proteins coming from the cultures. The proteins are expressed in arbitrary units of integration. This FIG. 3 illustrates the effective loading by proteins confirmed in the preparations (n=3) by measuring the levels of beta-actin between the wells; there are no statistical differences all along the culture. This figure represents the analyses by Slot Blots on 25 µg of total protein. The levels of beta-actin were measured using 3 preparations as internal standard, with control of the quantity of protein loaded per well.

FIG. 3A, in which the exocrine phenotype is revealed with antiamylase ▮, the ductal phenotype with anti-CK19 ▨, the endocrine phenotype with antichromogranin A ▦, illustrates the high levels of amylase protein expressed by the exocrine preparations after their isolation, while the levels of ductal (CK19) and endocrine (chromogranin A) proteins are lower. An extensive reduction of the amylase protein is observed after a day of culturing (92±3.3, p<0.05 versus day 1). FIG. 3B, with the anti-IPF-1 (mean±SEM, p<0.05 versus day 0), in which the intensity of the spots is expressed in arbitrary units after digital integration, illustrates slot blots which prove that the IPF-1 protein is present in minute levels in the exocrine preparations after isolation increase during their culture, and remain high. FIG. 3C shows the Western Blots representative of the five human pancreata, reveals that the 46 kd band characteristic of the IPF-1 protein is weak or undetectable immediately after isolation of the exocrine cells (day 0) and intensifies as the culture progresses. The Western Blot results are confirmed with two different anti-IPF-1 antibodies directed against the C-terminal and N-terminal domains. FIG. 3D illustrates the kinetic study obtained by using a more sensitive visualization with the ECL kit and a Phosphoimager® image analyzer, underlining the fact that this increase in the IPF-1 protein (3.2 fold) rapidly appears in the first two days of culture.

FIG. 4 shows the expression of the mRNA determined in the exocrine culture preparations (n=5), standardized for the expression of beta-actin.

FIG. 4A illustrates the PCR products with the specific bands of IPF-1 (262 bp) and of beta-actin (314 bp).

FIG. 4B illustrates that the average expression of IPF-1/ beta-actin is low before culturing and that it increases rapidly 10.5 fold after 3 days (n=5, p<0.001) with respect to day 1 and remains high, with levels of expression eight times higher after one week, and seven times higher after two weeks in comparison with day 1 (9 [sic; p]=0.08 versus day 1; p<0.001 versus day 0).

FIG. 4C, in which ▦ represents the expression of insulin standardized with respect to beta-actin (n=5; p>0.05) compared with day 0) and ▮ represents the expression of insulin from purified endocrine preparations (n=5), illustrates the determination of the mRNA of the insulin in the exocrine preparations in order to control the contamination with endocrine cell populations during culturing (islets (n=4, 71±6% pure) are used as positive control). The levels of mRNA in the exocrine cultures remain lower (for example, between 7% (day 0) and 2.5% (days 3, 7)) than those of the control islets. No significant differences between the levels of days 0, 3 or 7 were observed.

FIG. 5 illustrates the immunohistochemical analysis, complementary to the Slot blot, the Western Blot and the PCR-RT results, showing that the culturing of the exocrine preparations for one week leads to the loss of the specific immunolabeling of the amylase (not shown), and to an increase of the labeling of the ductal antigens CK19, CK7.

FIG. 5A illustrates that, after 7 days of culture, the cells show a ductal phenotype revealed with a dominant labeling for the expression of CK19. The labeling of the insulin is always negative in the exocrine preparations which were grown; consequently, the neuroendocrine marker chromogranin A was used for evaluating the contamination of the exocrine preparations with islets. FIG. 5B (arrow) illustrates that the contamination with endocrine cells is limited and remains lower than 5%, both in the initial preparations as well as at the end of culture. Double immunolabeling was done in order to establish that the majority of cells in the cultures derived from the exocrine preparations are ductal cells (CK19/CK7 positive cells) and IPF-1 positive cells either in the cytoplasmic compartment or in the nuclear compartment (CK7/IPF-1, illustrated in FIG. 5C). The rare IPF-1 positive and CK7 negative cells (arrowhead) probably correspond to contaminating beta-cells.

In order to exclude selective adherence of the exocrine tissue, the inventors compared the preparations immunolabeled with the amylase/Hoechst before day 0 and 12 h after the beginning of culture.

Approximately 60% (n=2, 59%±1 in triplicate) of all of the cells have [sic; typo] an amylase stain on day 0 (therefore 41% non-acinar) and this percentage remains the same after 12 h of culturing.

The apoptosis is monitored by immunolabeling with an antiamylase antibody/Hoechst 33258 (n=2).

The nuclear signs of apoptosis were virtually absent from the exocrine cultures, in particular during the principal phenotypic change (day 3). On day 5, a small number of cells in culture have nuclei in the shape of a half moon, indicators of a process of apoptosis; however, they remain negative for the staining with annexin V, an early marker of apoptosis.

Inversely, double immunolabeling of the preparations after 12 h and after two days (n=2) for amylase and Ki-67, a nuclear antigen expressed during all the phases of the cell cycle with the exception of G0, shows that the majority of acinar cells constitute part of the growing fraction. After approximately 12 h of culture, 40% of all of the cells are acinar cells in the cell cycle (Amy+/Ki67+), 15% are acinar cells which are not in the cycle (Amy+/Ki-67−), 43% of the cells are nonacinar cells in the cycle (Amy−/Ki-67+); thus only 17% of the cells are in G0 phase of the cell cycle and are consequently Ki-67 negative. After two days of culture, when the expression of the amylase is still visible by immunohistochemical techniques and the levels of proliferation (tritiated thymidine) are close to the peaks, 51.5% of the cells are acinar cells (Amy+/Ki-67−), 42% of the cells are nonacinar cells in the cycle (Amy−/Ki-67+).

The role of the IPF-1 transcription factor in the neogenesis of the islets is supported by its increased expression in the pancreatic ducts, the site of the endocrine cell precursors, in several models of pancreatic regeneration. The expression of the factor IPF-1 in recently divided ductal cells is based on the hypothesis that all the adult ductal cells can recover their pluripotentiality (for example, their stem cell capacity) (Bonner-Weir S. et al. "Partial pancreatectomy as a model of pancreatic regeneration" in Pancreatic Growth and Regeneration. Sarvetnick N. Ed. Paris, Karger Landes Systems, 1997, pp. 138–153).

The decisive role of the factor IPF-1/PDX-1 in the endocrine cell differentiation of digestive endodermal cells was recently confirmed in the liver (Ferber S. et al. Pancreatic duodenal homeobox gene 1 induces expression of insulin genes in liver and ameliorates streptozotocin induced hyperglycemia. Nature Med 6:568–572, 2000).

The transition of the exocrine cell preparations in culture to a ductal phenotype has been well characterized in various species, but the exact mechanism involved in it remains controversial. Ligation of the rat duct is followed by an apoptotic deletion of the acinar cells simultaneously with a proliferation of ductal cells. Logsdon et al., working on acinar cells of mice, also showed a substantial loss of exocrine tissue (DNA, proteins) preceding the cell proliferation.

Inversely, in experiments conducted by the inventors in the context of the present invention, the rapid increases of cell proliferation, of the levels of DNA and of protein observed immediately after cell attachment (12 h) correlate with the initial increase of the ductal cell markers and with the decrease of the level of amylase.

A selective attachment of the ductal cells and death and/or apoptosis of the acinar cells cannot explain these facts in the human model, because the proportion of amylase positive cells initially present in the preparations remains the same after 12 h of culture when the plates are cleaned of the unattached cells. Alternatively, this rapid loss of amylase may be due to a reduction of the levels of amylase in the acinar cells.

None of the methods used to evaluate the apoptosis, including early and later markers, detects increasing levels of apoptosis during the phenotypic transition (day 3).

In contrast, the early presence of Ki-67/amylase positive cells in the cultures invokes their potential proliferation and confirms that the phenotypic transition happens with the cell proliferation as demonstrated using other models.

The appearance of a small number of nuclei with a half moon shape is observed only after 5 days of culture, after the principal phenotypic transition. The absence of significant apoptosis in these cultures and the presence of high levels of proliferation proves that the acinar cells have dedifferentiated into cells with a ductal phenotype, simultaneously with the rapid growth of the preexisting CK19 positive cells.

These ductal cells derived from exocrine populations express low or nonexistent levels of protein IPF-1 as well as low levels of IPF-1 mRNA which increase rapidly during culture. The 46 kd band characteristic of IPF-1 is confirmed by two anti-IPF antibodies; in order to exclude detection by these sensitive techniques of IPF-1 derived from minimal fractions of contaminating endocrine cells, simultaneous quantifications of insulin mRNA were made. The levels of this insulin mRNA are initially detectable in the preparations when they are compared with the levels found for the islets, and remain practically constant during the whole culture period.

The immunohistochemistry with two anti-IPF-1 antibodies locates the expression of IPF-1 on the ductal cells (CK-7 positive). Only a few endocrine cells are present (FIG. 5). Using pan-neuroendocrine markers including chromogranin A and synaptophysin, the total number of endocrine cells in the initial preparation is estimated to be 4.7±1.8% of the initial preparation and 3.5±0.8% of the cells after 7 days of culture (results not shown).

The disagreement between this low (<5%) endocrine contamination of the exocrine cultures and the intensity of the IPF-1 and CK19 (CK7) immunolabeling contributes towards confirming that the factor IPF-1 does not come essentially from the CK19 negative contaminating beta-cells. The studies of double labeling with IPF-1 and synaptophysin (not shown) confirm these data.

The Western Blots done with extracts of total proteins isolated from purified human islets show the two forms of proteins with the visualization of two bands at 31 kd and 46 kd (data not shown), revealed with the antibody directed against the N-terminal domain of PDX-1. The protein extracts from preparations of human exocrine cell cultures show a principal 46 kd band and a weak or undetectable 31 kd cytoplasmic band.

Unlike the IPF-1 positive but CK19 negative cells shown by Beattie et al., which are of endocrine origin, the majority of cells in the cultures derived from the exocrine cells show a ductal phenotype (positive for CK19, CK7 and carbohydrate 19-9 (results not shown) and are simultaneously IPF-1 positive. The initial cultures shown by Beattie et al. were insulin and IPF-1 positive, quite unlike the cells described in the experiments conducted in the context of the present invention, implying that the IPF-1 positive cells of their study are dedifferentiated beta-cells.

Thus, the inventors show that the rapid dedifferentiation/transdifferentiation of exocrine cells in vitro is associated simultaneously with an increase of the ductal markers and with transcription of the factor IPF-1 at the mRNA level as well as at the protein level.

What is claimed is:

1. A process for obtaining mammalian insulin secreting cells in vitro, comprising:
   a) preparing mammalian pancreatic tissues from a previously removed pancreas;
   b) dissociating the pancreatic tissues into isolated pancreatic cells;
   c) eliminating endocrine cells from the isolated pancreatic cells to obtain exocrine cells;
   d) inducing dedifferentiation of the exocrine cells into ductal precursor cells; and
   e) inducing redifferentiation of the ductal precursor cells into insulin secreting cells, wherein the elimination of endocrine cells in part (c) is carried out by means of density gradient centrifugation, and wherein exocrine cells devoid of endocrine cells are recovered in a pellet as a result thereof.

2. A process according to claim 1, wherein the dissociation of the pancreatic tissues is carried out by enzymatic digestion.

3. A process according to claim 1, wherein the elimination of the endocrine cells is carried out by withdrawal of a fraction of the endocrine cells recovered in a density range between 1.027 g/L to 1.104 g/L.

4. A process according to claim 1, wherein the elimination of the endocrine cells is carried out by withdrawal of a fraction of the endocrine cells recovered in a density range between 1.045 g/L to 1.097 g/L.

5. A process according to claim 1, wherein the dedifferentiation further comprises:
   i) culturing the isolated pancreas cells obtained after the elimination of endocrine cells for a duration of between 4 to 9 days, with a cell concentration between $1 \times 10^6$ and $10 \times 10^6$ cells/mL, in a culture medium containing glucose at a concentration between 1 and 10 g/l, and a mixture of insulin, transferrin, and selenium at a concentration between 0.2 and 3%; and
   ii) recovering ductal precursor cells.

6. A process according to claim 5, wherein the cells are cultured with a cell concentration between $2 \times 10^6$ and $6 \times 10^6$ cells/ml.

7. A process according to claim 5, wherein the glucose is at a concentration between 2 and 5 g/l.

8. A process according to claim 5, wherein the mixture of insulin, transferrin, and selenium is used at a concentration between 1.0 and 2.5%.

9. A process according to claim 5, wherein the cells are cultured for a duration between 5 to 7 days.

10. A process according to claim 5, wherein the culture medium further contains serum, wherein the serum is fetal calf serum, bovine serum or human serum, and wherein the serum concentration is greater than 8%.

11. A process according to claim 10, wherein the serum is at a concentration between 10 and 15% final volume.

12. A process according to claim 5, wherein the culture medium further contains factors preventing the growth of fibroblasts, wherein the factors are present at a concentration between 20 and 100 µg/ml.

13. A process according to claim 12, wherein the factors preventing the growth of fibroblasts are at a concentration between 30 and 60 µg/ml.

14. A process according to claim 5, wherein the culture medium further contains antibiotics and/or antifungal agents.

15. A process according to claim 1, wherein the induction of redifferentiation further comprises:
   i) separating the ductal precursor cells to obtain separated ductal precursor cells;
   ii) culturing the separated ductal precursor cells for a duration between 12 and 36 hours, at cell concentration between $3.5 \times 10^5$ cells/25 cm$^2$ and $4 \times 10^6$ cells/25 cm$^2$, in a culture medium containing glucose at concentrations between 1 and 10 g/L;
   iii) withdrawing said culture medium to obtain non-adherent cells;
   iv) culturing the non-adherent cells for a duration between 4 and 12 days, in a culture medium containing glucose at a concentration between 1 and 10 g/L to obtain insulin secreting endocrine cells; and
   v) recovering the insulin secreting cells.

16. A process according to claim 15, wherein the separated ductal precursor cells are cultured at a concentration between $7 \times 10^5$ cells/25 cm$^2$ to $3 \times 10^6$ cells/25 cm$^2$.

17. A process according to claim 15, wherein the culture medium contains glucose at a concentration between 2 and 5 g/l.

18. A process according to claim 15, wherein the culture medium contains serum, wherein the serum is fetal calf serum, bovine serum or human serum at a concentration greater than 2.5% of final volume.

19. A process according to claim 18, wherein the serum is at a concentration between 5 and 15% final volume.

20. A process according to claim 15, wherein the culture medium contains a mixture of insulin, transferrin, and selenium, at a concentration between 0.2 and 5%.

21. A process according to claim 20, wherein the mixture of insulin, transferrin, and selenium is at a concentration between 0.5 and 2%.

22. A process according to claim 15, wherein the culture medium contains antibiotics and antifungal agents.

23. A process according to claim 15, wherein the ductal precursor cells are cultured in the presence of a matrix.

24. A process according to claim 15, wherein the culture medium contains growth factors.

25. A process according to claim 15, wherein the ductal precursor cells are cultured for a duration between 5 and 10 days.

26. A process according to claim 15, wherein the separation of the ductal precursor cells is done with trypsin at a concentration between 0.01 and 0.1% and EDTA at a concentration between 0.1 and 1 mM.

27. A process according to claim 15, wherein the trypsin is at a concentration between 0.015 and 0.03% and the EDTA is at a concentration between 0.25 and 0.75 mM.

28. A process according to claim 23, wherein the matrix is collagen type IV, 804G, collagen type I, or Matrigel.

29. A process according to claim 1, wherein the pancreatic tissues are obtained from a previous removal of a fragment of a pancreas of a brain dead adult human.

30. A process according to claim 1, wherein the pancreatic tissues are obtained from a previous removal of a fragment of a pancreas of a living patient suffering from a pancreatic pathology.

31. A process according to claim 1, wherein the pancreatic tissues are obtained from a previous removal of a fragment of a pancreas of a living patient suffering from diabetes.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: artificial sequence
<220> FEATURE:
<223> OTHER INFORMATION: Artificial sequence are primer designed to amplify sequences
<220> FEATURE:
<221> NAME/KEY: primer
<222> LOCATION: (1)..(18)

-continued

<223> OTHER INFORMATION: primer to amplify IPF-1 factor

<400> SEQUENCE: 1
ccatggatga agtctacc                                                  18

<210> SEQ ID NO 2
<211> LENGTH: 19
<212> TYPE: DNA
<213> ORGANISM: artificial sequence
<220> FEATURE:
<223> OTHER INFORMATION: Artificial sequence are primer designed to
      amplify sequences
<220> FEATURE:
<221> NAME/KEY: primer
<222> LOCATION: (1)..(19)
<223> OTHER INFORMATION: primer to amplify IPF-1 factor

<400> SEQUENCE: 2
gtcctcctcc tttttccac                                                 19

<210> SEQ ID NO 3
<211> LENGTH: 18
<212> TYPE: DNA
<213> ORGANISM: artificial sequence
<220> FEATURE:
<223> OTHER INFORMATION: Artificial sequence are primer designed to
      amplify sequences
<220> FEATURE:
<221> NAME/KEY: primer
<222> LOCATION: (1)..(18)
<223> OTHER INFORMATION: Primer to amplify insulin

<400> SEQUENCE: 3
tgtgaaccaa cacctgtg                                                  18

<210> SEQ ID NO 4
<211> LENGTH: 17
<212> TYPE: DNA
<213> ORGANISM: artificial sequence
<220> FEATURE:
<223> OTHER INFORMATION: Artificial sequence are primer designed to
      amplify sequences
<220> FEATURE:
<221> NAME/KEY: artificial
<222> LOCATION: (1)..(17)
<223> OTHER INFORMATION: Primer to amplify insulin

<400> SEQUENCE: 4
cgtctagttg cagtagt                                                   17

<210> SEQ ID NO 5
<211> LENGTH: 19
<212> TYPE: DNA
<213> ORGANISM: artificial sequence
<220> FEATURE:
<223> OTHER INFORMATION: Artificial sequence are primer designed to
      amplify sequences
<220> FEATURE:
<221> NAME/KEY: primer
<222> LOCATION: (1)..(19)
<223> OTHER INFORMATION: Primer to amplify beta-actin

<400> SEQUENCE: 5
atcatgtttg agacctcca                                                 19

<210> SEQ ID NO 6
<211> LENGTH: 20
<212> TYPE: DNA
<213> ORGANISM: artificial sequence -continued

```
<220> FEATURE:
<223> OTHER INFORMATION: Artificial sequence are primer designed to
      amplify sequences
<220> FEATURE:
<221> NAME/KEY: primer
<222> LOCATION: (1)..(20)
<223> OTHER INFORMATION: primer to amplify beta-actin

<400> SEQUENCE: 6
catctcttgc tcgaagtcca                                               20
```